(12) United States Patent
Min

(10) Patent No.: US 11,147,980 B2
(45) Date of Patent: Oct. 19, 2021

(54) METHOD AND DEVICE FOR MONITORING LEFT VENTRICULAR HYPERTROPHY AND CALCULATING DEFIBRILLATION THRESHOLDS

(71) Applicant: Pacesetter, Inc., Sylmar, CA (US)

(72) Inventor: Xiaoyi Min, Camarillo, CA (US)

(73) Assignee: Pacesetter, Inc., Sylmar, CA (US)

( * ) Notice: Subject to any disclaimer, the term of this patent is extended or adjusted under 35 U.S.C. 154(b) by 335 days.

(21) Appl. No.: 16/382,072

(22) Filed: Apr. 11, 2019

(65) Prior Publication Data

US 2020/0324132 A1    Oct. 15, 2020

(51) Int. Cl.
| | |
|---|---|
| *A61N 1/39* | (2006.01) |
| *A61N 1/37* | (2006.01) |
| *A61N 1/368* | (2006.01) |
| *A61N 1/362* | (2006.01) |
| *A61N 1/365* | (2006.01) |
| *A61N 1/372* | (2006.01) |

(52) U.S. Cl.
CPC ......... *A61N 1/3943* (2013.01); *A61N 1/3706* (2013.01); *A61N 1/3956* (2013.01); *A61N 1/368* (2013.01); *A61N 1/3627* (2013.01); *A61N 1/36521* (2013.01); *A61N 1/37252* (2013.01)

(58) Field of Classification Search
CPC ............................ A61N 1/3956; A61N 1/3706
See application file for complete search history.

(56) References Cited

PUBLICATIONS

Do et al. "Predictors of Elevated Defibrillation Threshold with the Subcutaneous Implantable Cardioverter-Defibrillator" The Journal of Innovations in Cardiac Rhythm Management, 8 (2017), 2920-2929 (10 pages).
Seidl et al. "Stepped Defibrillation Waveform is Substantially more Efficient than the 50/50% Tilt Biphasic" Heart Rhythm Society (2006) 1547-5271/ (6 pages).
Shorofsky et al "Improved Defibrillation Efficacy with an Ascending Ramp Waveform in Humans" Heart Rhythm Society (2005) 1547-5271 (7 pages).

*Primary Examiner* — Alyssa M Alter
(74) *Attorney, Agent, or Firm* — The Small Patent Law Group LLC; Dean D. Small

(57) ABSTRACT

A method and system for managing an implantable medical device (IMD) based on left ventricular hypertrophy (LVH) are provided. The method collects cardiac activity (CA) signals from one or more implantable electrodes at corresponding sensing sites. The method utilizes one or more processors to perform identifying a characteristic of interest from the CA signals, analyzing the characteristic of interest from the CA signals to identify an LVH state indicative of at least one of an occurrence or degree of LVH experienced by the patient, calculating a DFT expectation based on the LVH state and determining, based on the DFT expectation, at least one of i) a defibrillation shock parameter or ii) a maximum energy capacity of the IMD for implant.

20 Claims, 8 Drawing Sheets

METHOD AND DEVICE FOR MONITORING LEFT VENTRICULAR HYPERTROPHY AND CALCULATING DEFIBRILLATION THRESHOLDS

BACKGROUND

Embodiments of the present disclosure generally relate to methods and devices for monitoring left ventricular hypertrophy and calculating defibrillation thresholds.

High voltage ventricular-tachy therapies are delivered by subcutaneous implantable cardioverter defibrillator (S-ICD) devices after the tachycardia episode is detected and classified. Currently marketed S-CD devices use a conventional bi-phasic capacitive discharge waveform that is delivered from a bank of multiple capacitors that are connected in series. Conventional S-CD devices deliver about 80 joules of energy in a single bi-phasic shock. In order to generate a high energy shock of 80 J, conventional S-ICD devices require a bank of large high voltage capacitors connected in series and typically charged to 800V-900V. The capacitor bank and battery are two of the larger components in S-CD devices and thus the overall size of the device is largely dependent on the space needed to house the capacitor bank and battery. For example, the space requirements of the capacitor bank and battery cause the S-ICD devices to be 60 cc, 70 cc or larger.

Conventional S-ICD devices continue to be large in size In order to have a maximum energy capacity sufficient to successfully defibrillate patients who exhibit a high defibrillation threshold (DFT). For many years, physicians have been programming the S-ICD to delivery the maximum energy output for defibrillation shocks so that only one VF induction and one shock is needed when performing DFT testing during an S-CD implant procedure. However, more than half of patients have much lower DFTs than the maximum device output and do not need to receive shocks at maximum outputs.

A need remains for a non-invasive approach for estimation of DFTs that will allow the device to be programmed near the patient's actual DFT with a safety margin and with a back-up at the maximum output if the shocks near the DFT fail. Today, no mechanism exists to predict a patient DFT accurately or to monitor changes in the patient DFT. Accordingly, all patients are generally implanted with a similarly sized device, namely an S-ICD that has a very high maximum energy capacity (80 J) sufficient to successfully defibrillate substantially all types of patients regardless of an individual patient's DFT. Also, most or all patients are implanted with the same size S-ICD with little or no regard for changes in an individual patient's DFT.

A need remains for methods and devices that produce an effective defibrillation therapy at a significantly reduced energy level to enable a significant size reduction in the subcutaneous implantable medical devices while allowing for potential increases in the DFT.

BRIEF SUMMARY

In accordance with embodiments herein, a method for managing an implantable medical device (IMD) based on left ventricular hypertrophy (LVH) is provided. The method collects cardiac activity (CA) signals from one or more implantable electrodes at corresponding sensing sites. The method utilizes one or more processors to perform identifying a characteristic of interest from the CA signals, analyzing the characteristic of interest from the CA signals to identify an LVH state indicative of at least one of an occurrence or degree of LVH experienced by the patient, calculating a DFT expectation based on the LVH state and determining, based on the DFT expectation, at least one of i) a defibrillation shock parameter or ii) a maximum energy capacity of the IMD for implant.

Optionally, determining may comprise determining, as the defibrillation shock parameter, an energy level of a defibrillation shock. The method may automatically adjust the energy level of the defibrillation shock from a medium voltage (MV) shock to a high voltage (HV) shock when the LVH state exceeds an LVH threshold. The one or more processors may be provided within the IMD. The identifying, analyzing, calculating and determining operations may be performed automatically by the one or more processors, after implantation, on a periodic basis to monitor progression of the LVH. The identifying, analyzing and calculating operations may be performed during an implantation procedure for implanting the S-IMD. The determining may comprise determining the maximum energy capacity of the IMD for implant. The method may select, based on the DFT expectation, between at least first and second S-IMDs may have corresponding different first and second maximum energy capacities.

Optionally, the implantable electrodes may be positioned at a V1 sensing site and a V5 or V6 sensing site. The method may determine cardiac dimensions of at least one of a heart or chest wall of the patient and may update the LVH state based on a characteristic of interest from the cardiac dimensions. The calculating the DFT expectation may be based in part on model simulations recorded in a database. The analyzing operation may utilize a Sokolov-Lyon Product to identify when a patient is experiencing LVH or not experiencing LVH as the LVH state.

In accordance with embodiments herein, a system for managing an implantable medical device (IMD) based on left ventricular hypertrophy (LVH) is provided. The system includes electrodes that are configured to collect cardiac activity (CA) signals from one or more implantable electrodes at corresponding sensing sites. One or more processors configured to identify a characteristic of interest from the CA signals, analyze the characteristic of interest from the CA signals to identify an LVH state indicative of at least one of an occurrence or degree of LVH experienced by the patient, calculate a DFT expectation based on the LVH state and determine, based on the DFT expectation, at least one of i) a defibrillation shock parameter or ii) a maximum energy capacity of the IMD for implant.

Optionally, the one or more processors may be further configured to determine, as the defibrillation shock parameter, an energy level of a defibrillation shock. The one or more processors may be further configured to automatically adjust the energy level of the defibrillation shock from a medium voltage (MV) shock to a high voltage (HV) shock when the LVH state exceeds an LVH threshold. The one or more processors may be provided within a subcutaneous implantable medical device (S-IMD). The identify, analyze, calculate and determine operations may be performed automatically by the one or more processors, after implantation, on a periodic basis to monitor progression of the LVH. The identify, analyze and calculate operations may be performed during an implantation procedure for implanting an implantable medical device (IMD). The determine may comprise determining the maximum energy capacity of the IMD for implant.

Optionally, the one or more processors may be further configured to select, based on the DFT expectation, between at least first and second IMDs may have corresponding different first and second maximum energy capacities. The implantable electrodes may be positioned at a V1 sensing site and a V5 or V6 sensing site. The one or more processors may be further configured to receive cardiac dimensions of at least one of a heart or chest wall of the patient and update the LVH state based on a characteristic of interest from the cardiac dimensions. The one or more processors may be further configured to calculate the DFT expectation based in part on model simulations recorded in a database. The one or more processors may be configured to perform the analyze operation utilizing a Sokolow-Lyon Product to identify when a patient is experiencing LVH or not experiencing LVH as the LVH state.

DETAILED DESCRIPTION

Figure 1:
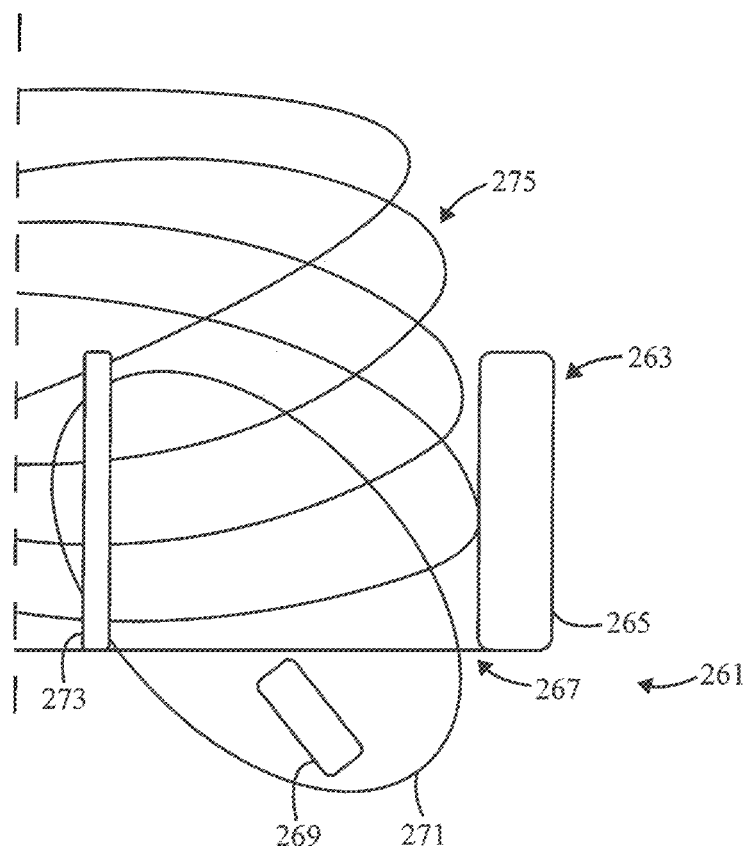
FIG. 1 illustrates a graphical representation of an implantable medical system that is configured to apply VF therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods and systems described herein may employ all or portions of structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, where indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "transvenous electrode" shall mean an electrode provide on a housing of a leadless IMD and/or an electrode provided on a lead inserted into or near a chamber of the heart (e.g., including leads inserted into the venous system along an exterior/interior of the heart). As non-limiting examples, transvenous electrodes may be located on a leadless IMD or a lead within an atrium or ventricle of the heart. The term transvenous electrode shall not include surface electrodes.

The term "subcutaneous electrode" shall mean an electrode provide on a housing of a subcutaneous IMD and/or an electrode provided on a lead inserted subcutaneously but not transvenously. As non-limiting examples, subcutaneous electrodes may be located on a SIMD, a parasternal lead, a lead extending along a posterior-anterior region of a patient's ribcage and the like. The term subcutaneous electrode shall not include surface electrodes.

The term "implantable electrode" shall include transvenous electrodes and subcutaneous electrodes, but shall not include surface electrodes.

The term subcutaneous sensing vector shall mean a sensing vector defined between two or more subcutaneous electrodes.

The term transvenous sensing vector shall mean a sensing vector defined between two or more transvenous electrodes.

The term "proxy", as used in connection with CA signals, shall refer to cardiac activity signals that have been collected by a subcutaneous or transvenous electrode and combined from one or more sensing vector in a manner to substantially simulate cardiac activity signals sensed along a sensing vector associated with a 12 lead surface ECG system. For example, a proxy CA signal, representing a proxy or estimate for a surface ECG surface vector, may be generated by combining a weighted combination CA signals from two or more subcutaneous sensing vectors.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the S-IMD and a local external device, and/or iii) receiving the data, signals, information, etc. at a remote server over a network connection. The obtaining operation, when from the perspective of an S-IMD, may include sensing new signals in real time, and/or accessing memory to read stored data, signals, information, etc. from memory within the S-IMD. The obtaining operation, when from the perspective of a local external device, includes receiving the data, signals, information, etc. at a transceiver of the local external device where the data, signals, information, etc. are transmitted from an S-IMD and/or a remote server. The obtaining operation may be from the perspective of a remote server, such as when receiving the data, signals, information, etc. at a network interface from a local external device and/or directly from an S-IMD. The remote server may also obtain the data, signals, information, etc. from local memory and/or from other memory, such as within a cloud storage environment and/or from the memory of a workstation or clinician external programmer.

The terms "medium-voltage shock" and "MV shock" refer to defibrillation stimulus delivered at an energy level sufficient to terminate a defibrillation episode in a heart, wherein the energy level is defined in Joules, pulse width, and/or maximum charge voltage. A MV shock from an IMD with a transvenous lead will have a different maximum energy and/or charge voltage than an MV shock from a subcutaneous S-IMD with a subcutaneous lead. In connection with an IMD having a transvenous lead, the terms medium voltage shock and MV shock refer to defibrillation stimulation that has an energy level that is no more than 25 J, and more preferably 15 J-25 J and/or has a maximum voltage of no more than 500V, preferably between 100-475V and more preferably between 400V-475V. In connection with an S-IMD having a subcutaneous lead (e.g., parasternal or otherwise), the terms medium voltage shock and MV shock refer to defibrillation stimulation that has an energy level that is no more than 48 J, and more preferably 35 J-45 J and/or has a maximum voltage of no more than 750 V, preferably between 200V-750V and more preferably between 500V-750V.

The terms "high-voltage shock" and "HV shock" refer to defibrillation stimulus delivered at an energy level sufficient to terminate a defibrillation episode in a heart. In connection with an IMD having a transvenous lead, the energy level is defined in Joules to be 40 J or more and/or the energy level is defined in terms of voltage to be 750V or more. In connection with an S-IMD having a subcutaneous lead (e.g., parasternal or otherwise), the terms high voltage shock and HV shock refer to defibrillation stimulation that has an energy level that 65 J or more, and more preferably 80 J and/or has a maximum voltage of more than 750V, and more preferably a voltage of 850V-1000V.

The term "LVH state" refers to a left ventricular hypertrophy condition currently experienced by a patient. The LVH state may be indicated as a binary state, namely either the presence/occurrence of LVH or the non-presence/non-occurrence of LVH. Additionally or alternatively, the LVH state may be indicated as a degree of LVH experienced by the patient along a scale (e.g., 0-10) ranging from little or no LVH to a substantial level of LVH.

The term "DFT expectation" refers to a calculation of a defibrillation threshold estimate or likelihood. The DFT expectation may also be referred to as a candidate DFT as the calculation represents an estimate or likelihood that a patient exhibits a particular defibrillation threshold or a defibrillation threshold within a select range. The DFT expectation and/or candidate DFT is based on a mathematical calculation, as described herein, which may or may not correspond to the patient's actual defibrillation threshold.

The term "defibrillation shock parameter" refers to parameters that define a shape and/or energy of a defibrillation shock waveform. Non-limiting examples of the parameters include a number of phases (e.g., monophasic, biphasic, more than two phases), energy level of a shock, initial/final voltage of a positive pulse in a biphasic shock, initial/final voltage of a negative pulse in a multi-phasic shock, and pulse width of each of the positive and negative pulses in a multi-phasic shock. As a further example, the defibrillation therapy may include more than one biphasic shock, in which case the parameters further include a designation of a number of shocks to deliver an interval between successive shocks and the like. As one example, the parameter may designate the energy level of a biphasic shock to have a medium energy level that is no more than 48 J, and more preferably 35 J-45 J. As another example, the parameter may designate an initial maximum voltage of a biphasic shock to have a medium voltage level that is no more than 750 V, preferably between 200V-750V and more preferably between 500V-750V.

The term "maximum energy capacity", when used to describe an S-IMD, refers to a maximum amount of energy that the S-IMD is capable of delivering in a defibrillation shock once the shocking capacitor bank is fully charged. For example, an S-IMD may have a medium level for a maximum energy capacity of 35 J-45 J, no more than 48 J. Alternatively, an S-IMD may have a high level for a maximum energy capacity of 50 J or more, and more preferably approximately 80 J.

The terms "V1", "V2", "V3", "V4", "V5", "V6", and the like are used throughout the application to refer sensing vectors and to positions on a patient's torso at which surface ECG electrodes are commonly positioned for a 12 lead ECG system. The terms "V1", "V2", "V3", "V4", "V5", "V6", "aVL", "aVF", "aVR", and the like, may be used to describe electrode positions, sensing vectors and the like.

Overview

Embodiments may be implemented in connection with one or more implantable medical devices (IMDs). Non-limiting examples of IMDs include one or more of therapy devices, and/or alternative implantable medical devices. For example, the IMD may represent a cardiac monitoring device, pacemaker, cardioverter, cardiac rhythm management device, defibrillator and the like. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

In accordance with embodiments herein methods and systems are described that use an S-IMD system to sense subcutaneous cardiac activity signals along sensing vectors that can either correspond to, or can be converted as proxies for, sensing vectors of the 12 electrode surface ECG lead. The "proxy" cardiac signals are used for monitoring LVH, predicting progression of heart disease leading to higher DFTs, and providing warnings of the disease progression through a remote patient care system.

Conventional subcutaneous ICDs are bulkier than conventional transvenous ICDs (e.g., 70 cc or 60 cc vs. 30 cc). Also, the DFTs associated with conventional subcutaneous ICDs are much higher, as compared to DFTs for conventional transvenous ICDs, and thus, a maximum output required from a conventional subcutaneous ICD is much larger than the required output of a conventional transvenous ICD (e.g., 80 J vs 40 J). In accordance with embodiments herein, methods and systems calculate DFT predictions, and thus tailor the maximum output required from the subcutaneous ICD to the patients DFT. As explained hereafter, embodiments herein enable identification of patients who can use a subcutaneous ICD that has a maximum output of up to 40 J or 48 J.

Clinical results have shown that only a small percentage of patients with traditional transvenous ICDs have exhibited a DFT, at the time of implant, near the maximum ICD output of 40 J, while the mean DFT for patients implanted with transvenous ICDs were generally near 10 J. Improvements are being developed to lower DFTs in patients that may initially exhibit, at the time of implant, a higher DFT. As the DFTs are lowered, the maximum output of the ICD can similarly be reduced to a lower maximum output. Further, for patients with low DFTs at implant, progression of cardiac disease could elevate DFTs higher until reaching a level sufficient to create a risk factor at a maximum output of the ICD.

In accordance with embodiments herein, prior to or at the time of implant, a patient specific defibrillation system (transvenous IMD or S-IMD) may be selected based on measurements and analysis described herein. For example, methods herein may predict high DFTs based on surface ECG measurements and patient anatomical characteristics. For example, surface ECG measurements may be analyzed utilizing a Sokolow-Lyon Product, alone or in combination with body and cardiac dimensions to provide DFT expectations (i.e., >25 J). Optionally, model simulations may be utilized to afford better accuracy for DFT expectations. For example, a database may be constructed from model simulations utilizing human body models and CA signal characteristics of interest. Measurements may be collected for a new patient and the new patient measurements can be extrapolated to a point in the data base to obtain a DFT expectation.

Additionally or alternatively, in accordance with embodiments herein, post implant monitoring may be provided. Following implant of a transvenous or subcutaneous IMD system, sensing electrodes of the system can be used to sense cardiac activity signals along sensing vectors that are similar to the sensing vectors utilized by a surface ECG lead (e.g., a 12 lead ECG configuration). The sensed cardiac activity signals are analyzed by one or more processors of the IMD (transvenous or subcutaneous), in connection with LVH monitoring and diagnosis, such as utilizing the Sokolow-Lyon Product method. The results of the LVH monitoring and diagnosis can be combined with stored patient anatomy data (e.g., updated via office follow up visits). The sensed cardiac activity signals may also be analyzed for other information of interest, such as the ST segment, QRS width for ischemia, HF and the like. When a patient's condition changes in a manner indicative of a potential risk for an elevated DFT, the S-IMD may issue a device warning, such as through a remote patient care system, and indicate that a physician's office visit is potentially warranted.

Additionally or alternatively, in accordance with embodiments herein, a tiered therapy may be managed based on the sensed cardiac activity signals and LVH progression. The tiered therapy may include at least first and second therapy tiers, at which associated shocks are delivered with different energy levels. For example, a first therapy tier may deliver one or more MV shocks, while a second therapy tier may deliver one or more HV Shocks. The S-IMD may be programmed with two or more therapy tiers, one of which is selected based on a DFT expectation calculated by the S-IMD based on the sensed cardiac activity signals. For example, while the sensed cardiac activity signals indicate LVH progression that satisfies a first criteria, when the patient exhibits a VF episode, the S-IMD may deliver one or more MV shocks corresponding to a first therapy tier. Alternatively, while the sensed cardiac activity signals indicate LVH progression that satisfies a second criteria, when the patient exhibits a VF episode, the S-IMD may deliver one or more HV shocks corresponding to a second therapy tier. In accordance with the foregoing, the S-IMD provides one or more shocks at a programmable energy level based on the indication of whether the LVH progression has increased the risk that the patient is experiencing an elevated DFT.

Implantable Medical Device

FIG. 1 illustrates a graphical representation of an implantable medical system 261 that is configured to apply VF therapy in accordance with embodiments herein. Embodiments may be implemented in connection with one or more subcutaneous implantable medical devices (S-IMDs). Non-limiting examples of S-IMDs include one or more of subcutaneous implantable cardioverter defibrillators (S-ICD). For example, the S-IMD may include one or more structural and/or functional aspects of the device(s) described in U.S. application Ser. No. 15/973,219, titled "IMPLANTABLE MEDICAL SYSTEMS AND METHODS INCLUDING PULSE GENERATORS AND LEADS", filed May 7, 2018; U.S. application Ser. No. 15/973,195, titled "SUBCUTANEOUS IMPLANTATION MEDICAL DEVICE WITH MULTIPLE PARASTERNAL-ANTERIOR ELEC- TRODES", filed May 7, 2018; which are hereby incorporated by reference in their entireties.

The system 261 includes a subcutaneous implantable medical device (S-IMD) 263 that is configured to be implanted in a subcutaneous area exterior to the heart. The S-IMD 263 is positioned in a subcutaneous area or region, and more particularly in a mid-axillary position along a portion of the rib cage 275. Optionally, the system 261 may also include a leadless pacemaker 269 implanted within the heart, such as at an apex 271 of the right ventricle. Optionally, the leadless pacemaker 269 may be omitted entirely. The system 261 does not require insertion of a transvenous lead.

The pulse generator 265 may be implanted subcutaneously and at least a portion of the lead 267 may be implanted subcutaneously. In particular embodiments, the S-IMD 263 is an entirely or fully subcutaneous S-IMD. Optionally, the S-IMD 263 may be positioned in a different subcutaneous region.

The S-IMD 263 includes a pulse generator 265 and at least one lead 267 that is operably coupled to the pulse generator 265. The lead 267 includes at least one electrode segment 273 that is used for providing MV shocks for defibrillation. Optionally, the lead 267 may include one or more sensing electrodes. The pulse generator 265 includes a housing that forms or constitutes an electrode utilized to deliver MV shocks. The electrode associated with the housing of the pulse generator 265 is referred to as the "CAN" electrode.

In an alternative embodiment, the lead 267 may include one or more electrode segments, in which the electrode segments are spaced apart from one another having an electrical gap therebetween. The lead body may extend between the gap. One electrode segment may be positioned along an anterior of the chest, while another electrode segment may be positioned along a lateral and/or posterior region of the patient. The electrode segments may be portions of the same lead, or the electrode segments may be portions of different leads. The electrode segments may be positioned subcutaneously at a level that aligns with the heart of the patient for providing a sufficient amount of energy for defibrillation. The lead includes a lead body that extends from the mid-auxiliary position along an inter-costal area between ribs and oriented with the coil electrode(s) extending along the sternum (e.g., over the sternum or parasternally within one to three centimeters from the sternum). A proximal end the coil electrodes may be located proximate to the xiphoid process.

Figure 2:
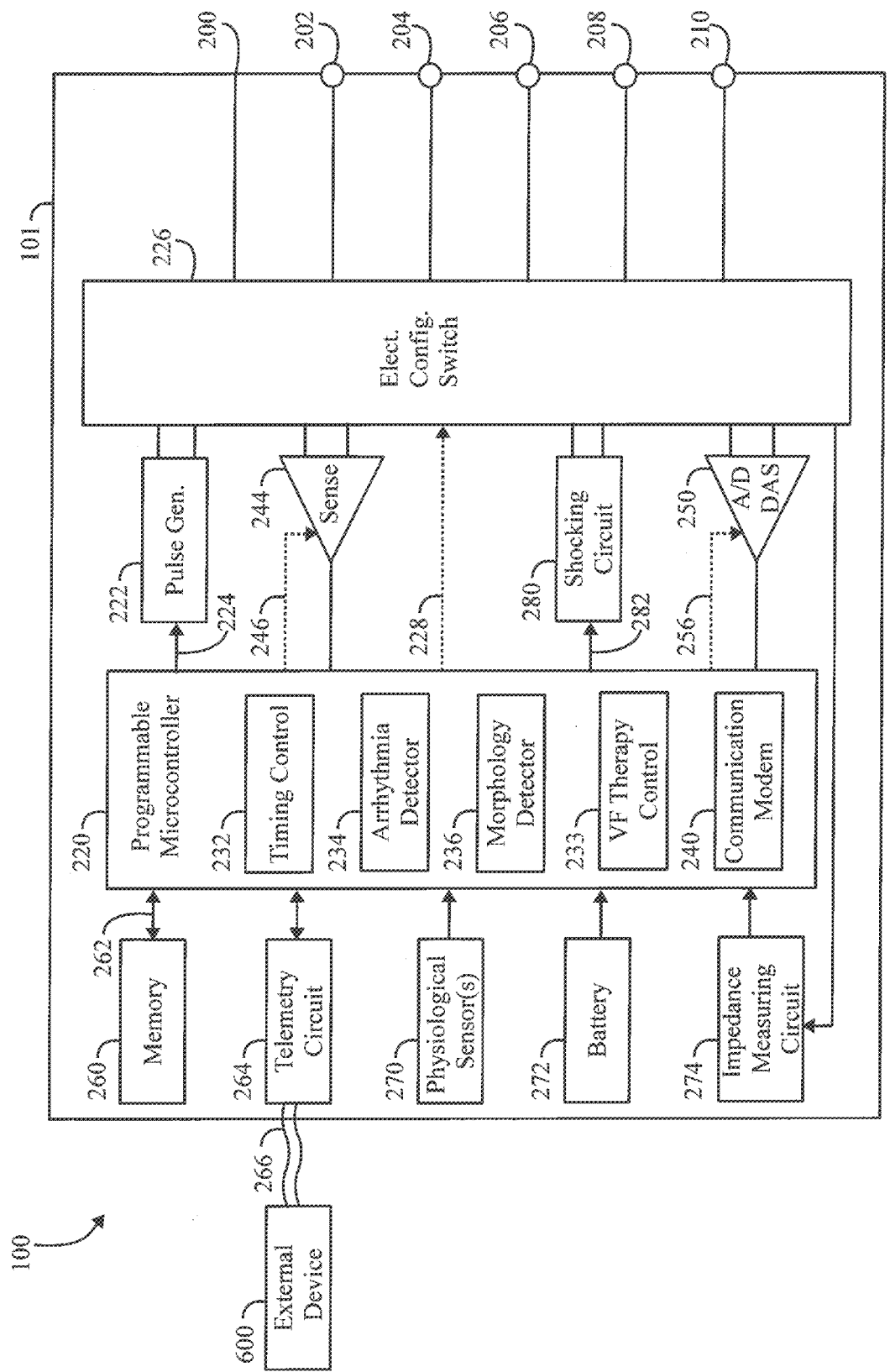
FIG. 2 shows a block diagram of an exemplary S-IMD that is configured to be implanted into the patient in accordance with embodiments herein.

FIG. 2 shows a block diagram of an exemplary S-IMD 100 that is configured to be implanted into the patient. The S-IMD 100 may treat both fast and slow arrhythmias with stimulation therapy, including cardioversion, pacing stimulation, an implantable cardioverter defibrillator, suspend tachycardia detection, tachyarrhythmia therapy, and/or the like.

The S-IMD 100 has a housing 101 to hold the electronic/ computing components. The housing 101 (which is often referred to as the "can," "case," "encasing," or "case electrode") may be programmably selected to act as the return electrode for certain stimulus modes. The housing 101 further includes a connector (not shown) with a plurality of terminals 200-210. The terminals may be connected to electrodes that are located in various locations within and about the heart. The type and location of each electrode may vary. For example, the electrodes may include various combinations of ring, tip, coil, shocking electrodes, and the like.

The S-IMD 100 includes a programmable microcontroller 220 that controls various operations of the S-IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The S-IMD 100 further includes a ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2A. Optionally, the S-IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The S-IMD 100 includes sensing circuit 244 selectively coupled to one or more electrodes that perform sensing operations, through the switch 226 to detect the presence of cardiac activity in the chamber of the heart 111. The output of the sensing circuit 244 is connected to the microcontroller 220 which, in turn, triggers, or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit 224.

In the example of FIG. 2A, the sensing circuit 244 is illustrated. Optionally, the S-IMD 100 may include multiple sensing circuits 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The S-IMD 100 further includes an analog-to-digital (A/D) data acquisition system (DAS) 250 coupled to one or more electrodes via the switch 226 to sample cardiac signals across any pair of desired electrodes. The A/D converter 250 is configured to acquire intracardiac electrogram signals, convert the raw analog data into digital data and store the digital data for later processing and/or telemetric transmission to an external device 600 (e.g., a programmer, local transceiver, or a diagnostic system analyzer). The A/D converter 250 is controlled by a control signal 256 from the microcontroller 220.

The switch 226 may be coupled to an LV lead having multiple LV electrodes, at least one of the LV electrodes configured to be located proximate to the LV site corresponding to the pacing site and to deliver the burst pacing therapy. The switch 226 may be further coupled to a second lead with at least one of a superior vena cava (SVC) coil electrode or an RV coil electrode, the shock vector including a CAN of the S-IMD and at least one of the SVC coil electrode or the RV coil electrode.

The microcontroller 220 is operably coupled to a memory 260 by a suitable data/address bus 262. The programmable operating parameters used by the microcontroller 220 are stored in the memory 260 and used to customize the operation of the S-IMD 100 to suit the needs of a particular patient. The operating parameters of the S-IMD 100 may be non-invasively programmed into the memory 260 through a telemetry circuit 264 in telemetric communication via communication link 266 (e.g., MICS, Bluetooth low energy, and/or the like) with the external device 600.

The S-IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the S-IMD 100, the physiological sensor(s) 270 may be external to the S-IMD 100, yet still, be implanted within or carried by the patient. Examples of physiological sensors might include sensors that, for example, sense respiration rate, pH of blood, ventricular gradient, activity, position/posture, minute ventilation, and/or the like.

A battery 272 provides operating power to all of the components In the S-IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the S-IMD 100 employs lithium/silver vanadium oxide batteries.

The S-IMD 100 further includes an impedance measuring circuit 274, which can be used for many things, including sensing respiration phase. The impedance measuring circuit 274 is coupled to the switch 226 so that any desired electrode and/or terminal may be used to measure impedance In connection with monitoring respiration phase. The S-IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The microcontroller 220 further controls a shocking circuit 280 by way of a timing control 232. The shocking circuit 280 generates shocking pulses, such as MV shocks, LV shocks, etc., as controlled by the microcontroller 220. In accordance with some embodiments, the shocking circuit 280 includes a single change storage capacitor that delivers entire phase I and phase II therapies. The shocking circuit 280 is controlled by the microcontroller 220 by a control signal 282. Optionally, the microcontroller 220 may generate the control signals described in connection with FIGS. 7 and 8 to shape MV and LV shocks.

Although not shown, the microcontroller 220 may further include other dedicated circuitry and/or firmware/software components that assist in monitoring various conditions of the patient's heart and managing pacing therapies. The microcontroller 220 further includes a timing control 232, an arrhythmia detector 234, a morphology detector 236 and multi-phase VF therapy controller 233. The timing control 232 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The timing control 232 controls a timing for delivering the phase I, II and III therapies in a coordinated manner. The timing control 232 controls the phase II and II therapy timed relative to the MV shocks to cooperate with the MV shocks to terminate fibrillation waves of the ventricular arrhythmia episode and to reduce a defibrillation threshold of the heart below a shock-only defibrillation threshold.

The morphology detector 236 is configured to review and analyze one or more features of the morphology of CA signals. For example, in accordance with embodiments herein, the morphology detector 236 may analyze the morphology of detected R-waves, where such morphology is then utilized to determine whether to include or exclude one or more beats from further analysis. For example, the morphology detector 236 may be utilized to identify non-conducted ventricular events, such as ventricular fibrillation and the like.

The arrhythmia detector 234 is configured to apply one or more arrhythmia detection algorithms for detecting arrhythmia conditions. By way of example, the arrhythmia detector 234 may apply various VF detection algorithms. The arrhythmia detector 234 is configured to declare a ventricular fibrillation (VF) episode based on the cardiac events.

The therapy controller 233 is configured to perform the operations described herein. The therapy controller 233 is configured to identify a multi-phase VF therapy based on the ventricular fibrillation episode, the multi-phase VF therapy including MV shocks, LV shocks and a pacing therapy. The therapy controller 233 is configured to manage delivery of the burst pacing therapy at a pacing site in a coordinated manner after the MV and LV shocks. The pacing site is located at one of a left ventricular (LV) site or a right ventricular (RV) site. The therapy controller 233 is configured to manage delivery of the MV shock along a shocking vector between shocking electrodes.

The therapy controller 233 is further configured to analyze a timing of VF beats to obtain at least one of a VF cycle length (CL) or variation and to determine at least one of a number of pulses in a pulse train of the burst pacing therapy or a duration of pulse train of the burst pacing therapy based on at least one of the VF cycle length or variation. The therapy controller 233 may be further configured to set a timing delay to time the burst pacing therapy such that one or more of pulses therefrom occur during a period of time in which a local tissue region surrounding the pacing site is excitable and not refractory. The therapy controller 233 may be configured to set a frequency of the burst pacing therapy at a high frequency relative to a cycle length of non-fibrillation arrhythmias.

In accordance with embodiments, the S-IMD 100 may represent a subcutaneous implantable cardioverter defibrillator (S-ICD). Optionally, the communication modem 240 may be configured to wirelessly communicate with a leadless pacemaker, such as to pass timing information therebetween. The S-ICD may deliver phase I and II therapies, while the phase III pacing therapy may be delivered by the S-CID or the leadless pacemaker. The communication modem 240 may transmit timing information to a leadless pacemaker such as when sending an instruction for the leadless pacemaker to deliver pacing therapies in connection with embodiments herein. The communication modem 240 may receive timing information from a leadless pacemaker such as when receiving a direction from the leadless pacemaker that the low voltage therapy has been delivered or is currently being delivered and that S-ICD should now deliver the HV shock(s).

Prediction of Left Ventricular Hypertrophy

Figure 3:
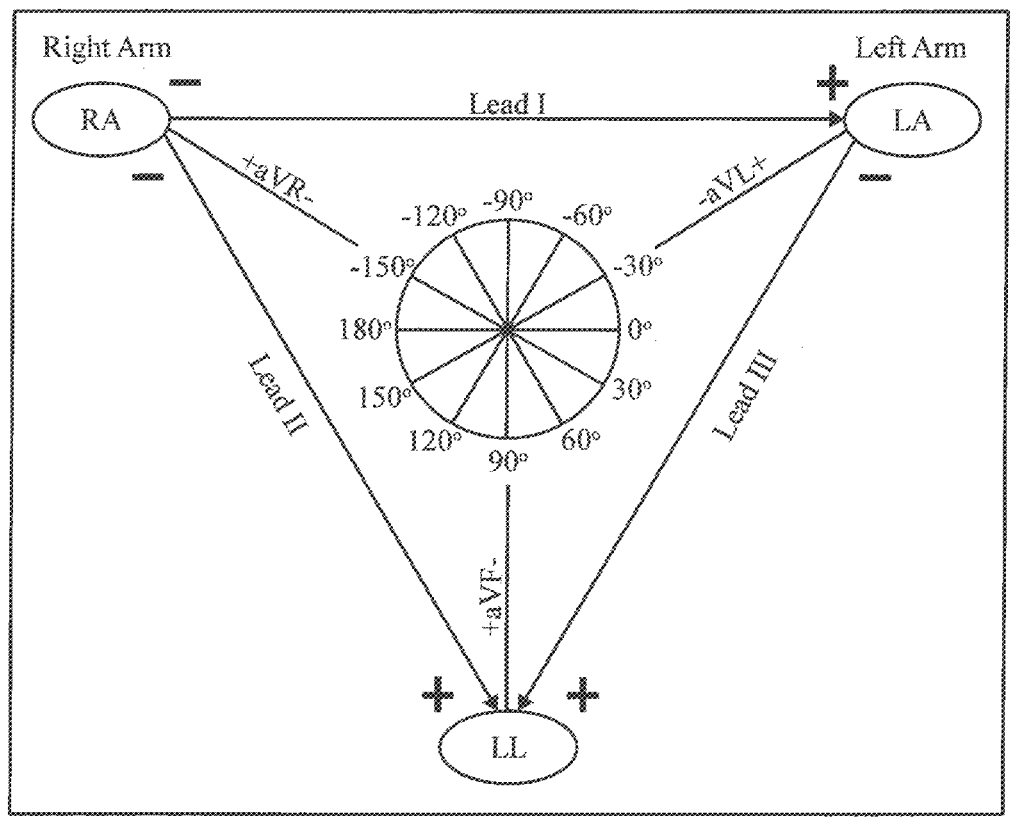
FIG. 3 illustrates a torso model of surface ECG sensing sites utilized in connection with a lead ECG lead system in accordance with embodiments herein.

FIG. 3 illustrates a torso model of surface ECG sensing sites utilized in connection with a 12 lead ECG lead system. The sensing sites may utilize combinations of electrodes that are arranged in various polarities to defined bipolar sensing vectors and unipolar sensing vectors. A bipolar sensing vector is defined by at least two electrodes of opposite polarity (one positive and one negative) or one positive electrode and a reference point. A unipolar sensing vector is defined by a single positive electrode and a reference point. For a routine analysis of the heart's electrical activity, an ECG recorded from 12 separate leads is used. A 12-lead ECG includes three bipolar limb leads (I, II, and III), three unipolar limb leads IV, V, and VI (also referred to as sensing vectors aVR, aVL, and aVF, respectively), and six unipolar chest leads, also called precordial or V leads, (V1, V2, V3, V4, V5 and V6).

Figure 4:
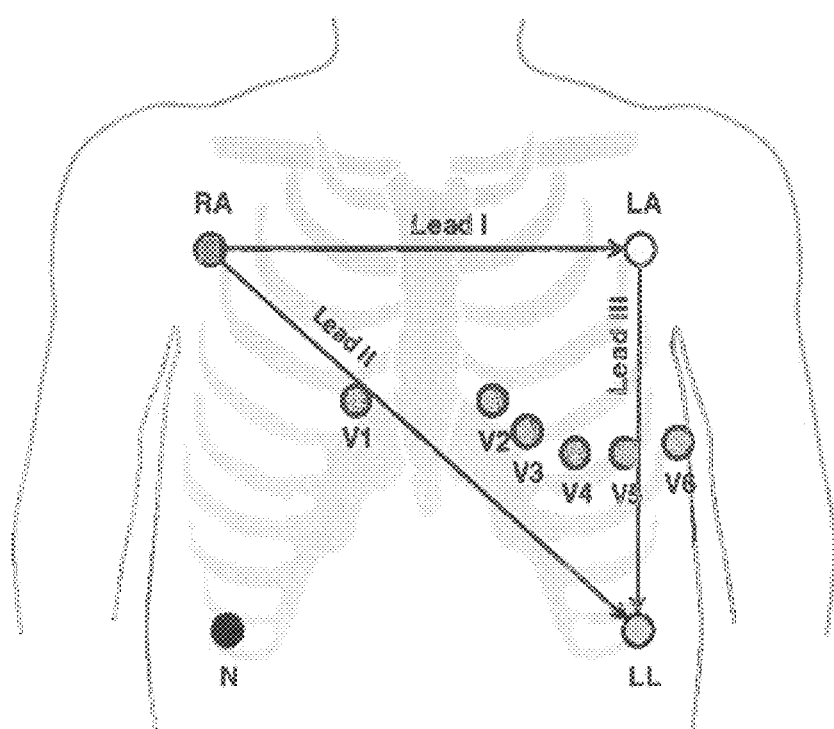
FIG. 4 illustrates a vector model for a portion of the sensing leads from the torso model of FIG. 3 in accordance with embodiments herein.

FIG. 4 illustrates a vector model for a portion of the sensing leads from the torso model of FIG. 3. The sensing vector associated with lead I (also referred to as the aVL electrode) provide cardiac activity signals, as viewed from the left arm and are indicative of cardiac activity at the lateral wall of the LV (also referred to as the aVL sensing site or vector). The sensing vectors associated with the leads II, III and aVF provide cardiac activity signals, as viewed from the left leg and are indicative of cardiac activity at the inferior wall of the LV (also referred to as the II, III and aVF sensing sites or vectors). The sensing vectors associated with the leads V5 and V6 provide cardiac activity signals, as viewed from the left lateral chest and are indicative of cardiac activity at the lateral wall of the LV (also referred to as the V5 and V6 sensing sites or vectors). The sensing vectors associated with the leads V3 and V4 provide cardiac activity signals, as viewed from the lateral anterior chest (also referred to as the V3 and V4 sensing sites or vectors). The sensing vectors associated with the leads V1 and V2 are provided along the sternal borders and provide cardiac activity signals as viewed through the right ventricle toward the septal wall (also referred to as the V1 and V2 sensing sites or vector). The 12-lead ECG system defines, among other things, a collection of sensing vectors from the center of the heart to the corresponding electrodes V1-V6, RA, LA and LL.

When the myocardium is hypertrophied, there is a larger mass of myocardium for electrical activation to pass through. Thus, an amplitude of a QRS complex, representing ventricular depolarization, is increased. Likewise, when the myocardium is abnormally thickened, and electrical activity takes longer to traverse throughout the whole heart, the duration of the QRS complex may be widened. This is referred to as "LVH with QRS widening." Also, repolarization may be affected via similar mechanisms that can result in abnormal ST segments or T waves. This is referred to as "LVH with strain" or "LVH with repolarization abnormality." At times, repolarization abnormalities can mimic ischemic ST changes. Accordingly, it is desirable to distinguish ischemic ST changes from the foregoing LVH related repolarization abnormalities that occur during a myocardial infarction. The typical pattern with LVH includes deviation of the ST segment in the opposite direction of the QRS complex (discordance), and a T-wave inversion pattern is present.

Over time, various criteria have been developed to diagnose LVH based on cardiac activity signals measured by a 12 lead ECG system. For example, the Cornell criteria utilize ECG signals from electrodes at the aVL position and V3 position on a surface ECG lead. The amplitude of the R-wave from the aVL electrode and the amplitude of the S-wave from the V3 electrode are added together. If the sum is greater than 28 millimeters in males or greater than 20 mm in females, the Cornell criteria would determine that LVH is present. The modified Cornell Criteria examine the R-wave from the aVL electrode alone. If the R-wave is greater than 12 mm in amplitude, LVH is determined to be present.

In accordance with the Sokolow-Lyon Criteria (SLC), the amplitude of the S-wave, as measured by the V1 electrode, is added to the amplitude of the R-wave as measured at the V5 or V6 electrode. If the sum is greater than 35 mm, the SLC determine LVH to be present. In accordance with a Romhilt-Estes LVH Point Scoring System (RE Scoring System), a score is determined (from the factors noted below). If the score equals 4, the RE Scoring System determines LVH to be present with 30% to 54% sensitivity. If the score is greater than 5, the RE Scoring System determines LVH to be present with 83% to 97% specificity. The RE Scoring System uses the following criteria:

Amplitude of largest R or S in limb leads≥20 mm=3 points

Amplitude of S in V1 or V2≥30 mm=3 points

Amplitude of R in V5 or V6≥30 mm=3 points

ST and T wave changes opposite QRS without digoxin=3 points

ST and T wave changes opposite QRS with digoxin=1 point

Left Atrial Enlargement=3 points

Left Axis Deviation=2 points

QRS duration≥90 ms=1 point

Intrinsicoid deflection in V5 or V6>50 ms=1 point

Another method for predicting high DFT patients is the Sokolow Lyon Product (SLP) developed by Bruce Lerman's group at Cornell University. The Sokolow-Lyon Product represents a product of a voltage and a QRS duration. More specifically, the cardiac activity signals measured at the V1 electrode and either of the V5 or V6 electrodes are analyzed to identify a peak voltage of the R-wave. The peak voltages of the R-wave are summed for the V1 and V5 electrodes, or for the V1 and V6 electrodes. The sum of V1+V5 voltage (or V1+V6 voltage) is then multiplied by the duration of the QRS complex to form the SLP. The SLP represents a good predictor for the LVH state, namely whether LVH is present or not. For example, the SLP provides a predictor for the LVH state by comparing the SLP to an LVH threshold (e.g., 300). When the SLP exceeds the LVH threshold, this provides a good indication that the patient will exhibit a higher DFT, namely a DFT above a DFT threshold that is set at a level between MV shocks and HV shocks (e.g., a DFT of >25 J).

As a non-limiting example, the SLP voltage sums may be between 500 uV-5000 uV, while the QRS duration may be between 50 msec and 200 msec, continuing the foregoing example, the SLP may range from 25 uV-sec to 1000 uV-sec. As further non-limiting examples, the voltages and QRS durations may be further divided for patients having DFTs above and below a DFT threshold (e.g., 25 J). For example, patients having a DFT below 25 J may exhibit voltage sums between 500 uV and 3500 uV, and QRS durations between 50 ms and 400 ms. Patients having a DFT threshold above 25 J may exhibit voltage sums between 1500 uV and 5000 uV, and QRS durations between 100 ms and 200 ms. Continuing the foregoing examples, patients having a DFT below 25 J may exhibit an SLP in the range of 25 uV-sec to 300 uV-sec. Patients having a DFT above 25 J may exhibit an SLP in the range of 300 uV-sec to 1000 uV-sec.

Prior clinical results have shown that the statistical difference for the Sokolow-Lyon Product (for patients with DFTs>25 J versus patients with DFTs<25 J) was significant while other parameters such as left ventricular ejection fraction (LVEF) were not significantly different between patients with DFTs<25 J and patients with DFTs>25 J. Monophasic and biphasic defibrillation waveforms have been tested, and a percentage of patients with DFTs>25 J were almost the same. However, the difference in the SLP was bigger when utilizing a biphasic waveform as compared to the SLP when using a monophasic waveform. In accordance with at least one clinical study, when the probability of DFTs>25 J was tested according to Textiles of Sokolow-Lyon Product, the probability of DFT>25 J was zero if SLP was less 202, about 20% if SLP was between 202 and 302, and 34% if SLP was greater than 302. Given the foregoing, left ventricular hypertrophy can be diagnosed with good specificity based on cardiac activity signals measured along select sensing vectors between certain combinations of electrodes located at predetermined subcutaneous sensing sites.

In accordance with embodiments herein, transvenous and/or subcutaneous sensing sites are defined to operate as proxies or substitutes for the sensing sites of an ECG lead system utilizing surface electrodes attached to an exterior of the patient's skin at the sensing sites noted in connection with FIGS. 3, 4A and 4B.

FIG. 4B illustrates a vector model for a portion of the sensing leads from the torso model of FIGS. 3 and 4A, with the addition of subcutaneous electrodes for a pectoral CAN to long or segmented anterior posterior coil lead. The positions V1-V6, and markers aVR, aVL, aVF, I, II, III, correspond to the same positions in FIGS. 3, 4A and 4B, however, FIG. 4B adds subcutaneous sensing positions V7, V8 and V9 for a segmented anterior posterior coil.

Methods and systems herein perform a calibration operation in which electrode configurations and sensing vectors available at a given IMD (transvenous and/or subcutaneous) are correlated to the sensing vectors of the 12 lead ECG system. For example, S-IMD sensing vectors may be calibrated/correlated to the 12 lead ECG sensing vectors at a patient visit to a clinician, during an implant procedure, pre-implant, and the like. Additionally or alternatively, the S-IMD sensing vectors may be calibrated/correlated to the 12 lead ECG sensing vectors through computer modeling there between. More generally, one or more sensing vectors from a transvenous or subcutaneous lead may be analyzed manually or automatically to determine combinations of sensing vectors and weighting factors to be applied to the sensing vectors that generate a desired proxy CA signal. For example, when an S-IMD system includes a parasternal electrode and a mix-auxiliary CAN electrode, the combination may be used to define a set of subcutaneous sensing vectors that can be used to obtain a potential at a center of the heart (e.g., as half of the potential different between the parasternal coil electrode and the CAN electrode=parasternal coil+mid-auxiliary CAN)/2). The subcutaneous sensing vector may be correlated positions of surface ECG electrodes V1-V6, RA, LA and LL noted in FIG. 4. As a further example, the subcutaneous sensing vector $V_{sub\_1}$ may be calculated as $V_{sub\_1}$=V1−(parasternal coil+mid-auxiliary CAN)/2.

A difference of V1/V2 and V5/V6 could be indicative of propagation along the septal wall, while a difference of V5/V6 and V8/V9 can be used for propagation in the posterior LV wall. Proxy CA signals may be determined that also indicated propagation along the septal wall and the posterior LV wall. For example, with a transvenous lead, a sensing vector between the LV electrodes to the RV coil, or RV coil/SVC coil to RV tip can be used to measure LV wall or septal thickness. As another example, a sensing vector from the RV coil/SVC coil to the IMD CAN can be used to measure septal thickness or LV mass, while a sensing vector between the IMD CAN to RV tip or ring can be used to measure posterior LV wall thickness. The foregoing sensing vectors can be used to define proxy sensing vectors and/or proxy CA signals that are used (as described herein) to determine LVH and DFT expectations.

Figure 5A:
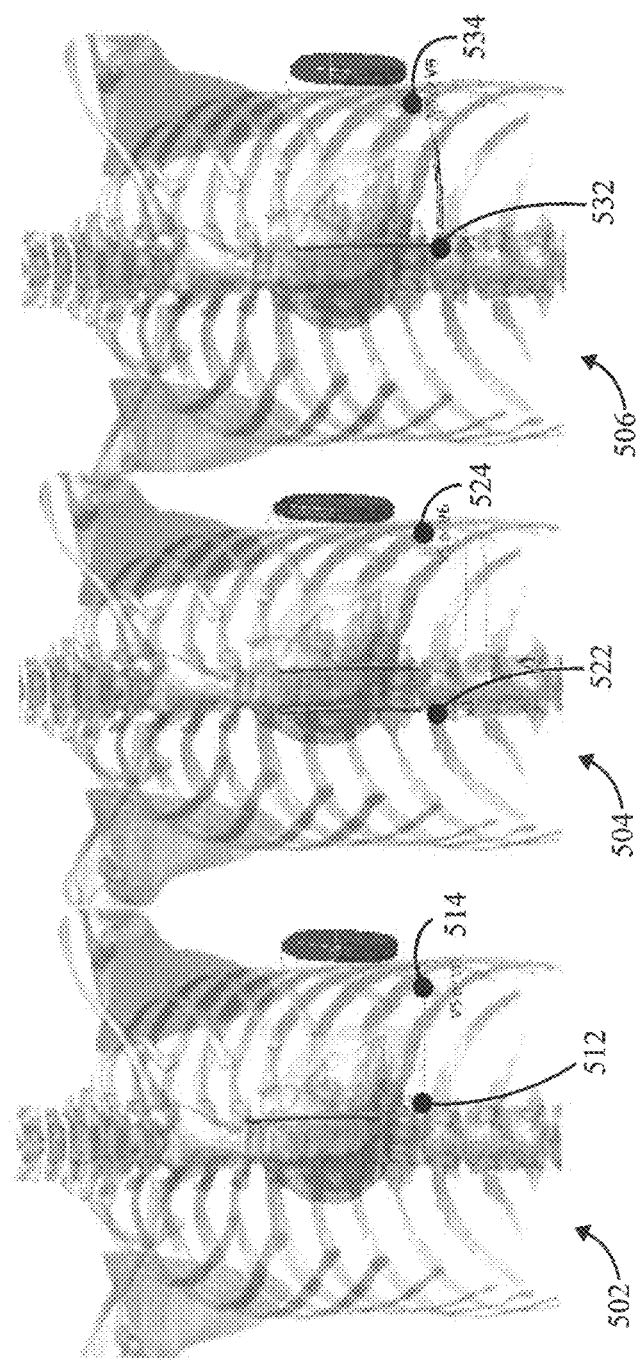
FIG. 5A illustrates examples for positions at which subcutaneous electrodes and a mid-auxiliary positioned subcutaneous S-IMD may be implanted in accordance with embodiments herein.

FIG. 5A illustrates examples for positions at which subcutaneous electrodes and a mid-auxiliary positioned subcutaneous S-IMD may be implanted in accordance with embodiments herein. The S-IMD system at 502 includes a single parasternal coil lead arranged to have a shocking coil positioned to extend along the sternum and an S-IMD located at a mid-axillary position. The S-IMD system at 504 includes dual parasternal shocking coils, provided on separate parasternal leads or a common parasternal lead. The parasternal coils are arranged to extend along opposite sides of the sternum and an S-IMD located at the mid-axillary position. The S-IMD system at 506 includes a single parasternal coil lead with a shocking coil arranged to extend along one side of the sternum, with an anterior coil and an S-IMD located at the mid-axillary position.

FIG. 5A also illustrates subcutaneous sensing sites that may be utilized as proxies or substitutes for the surface electrode sensing sites of a 12 lead ECG system. In the configuration at 502, the parasternal coil lead may include a sensing electrode 512 located at a substantially similar position to the V1 electrode of a 12 lead ECG system. The sensing electrode 512 may be provided proximate to the distal end of the parasternal coil lead and configured to be electrically isolated from the shocking coil. Optionally, the sensing electrode may be provided on a separate sensing lead extending from the S-IMD. A sensing electrode 514 is also provided at an intermediate point along the parasternal coil lead. The sensing electrode 514 is located at a substantially similar position to the V5 or V6 electrode of the 12 lead ECG system. The sensing electrode 514 may be provided at an intermediate point along the parasternal coil lead and configured to be electrically isolated from the shocking coil. Optionally, the sensing electrode 514 may be provided on a separate sensing lead extending from the S-IMD. Optionally the sensing electrodes 514 and 512 may be provided on a common sensing lead that is separate from the parasternal coil lead.

The configuration at 504 includes sensing electrodes 522 and 524 located at substantially similar positions (or proxy sensing vectors) to the V1 and V5/V6 electrodes of the 12 lead ECG system. The sensing electrodes 522 and 524 may be provided at corresponding points along a parasternal coil lead and/or provided within a separate sensing lead.

The configuration at 506 includes sensing electrodes 532 and 534 located at substantially similar positions (or proxy sensing vectors) to the V1 and V5/V6 electrodes of the 12 lead ECG system. The sensing electrodes 532 and 534 may be provided a corresponding points along a parasternal coil lead and/or provided within a separate sensing lead.

Additionally or alternatively, the sensing electrode may be positioned at the proximal end of the sternal shocking coil at a position substantially similar to the V2 electrode of the 12 lead ECG system or to define a proxy sensing vector similar to the sensing vector associated with the V2 electrode. Additionally or alternatively, in the event that the S-IMD is located near the V5 or V6 electrode positions, a sensing electrode may be provided on the housing of the S-IMD.

Figure 5B:
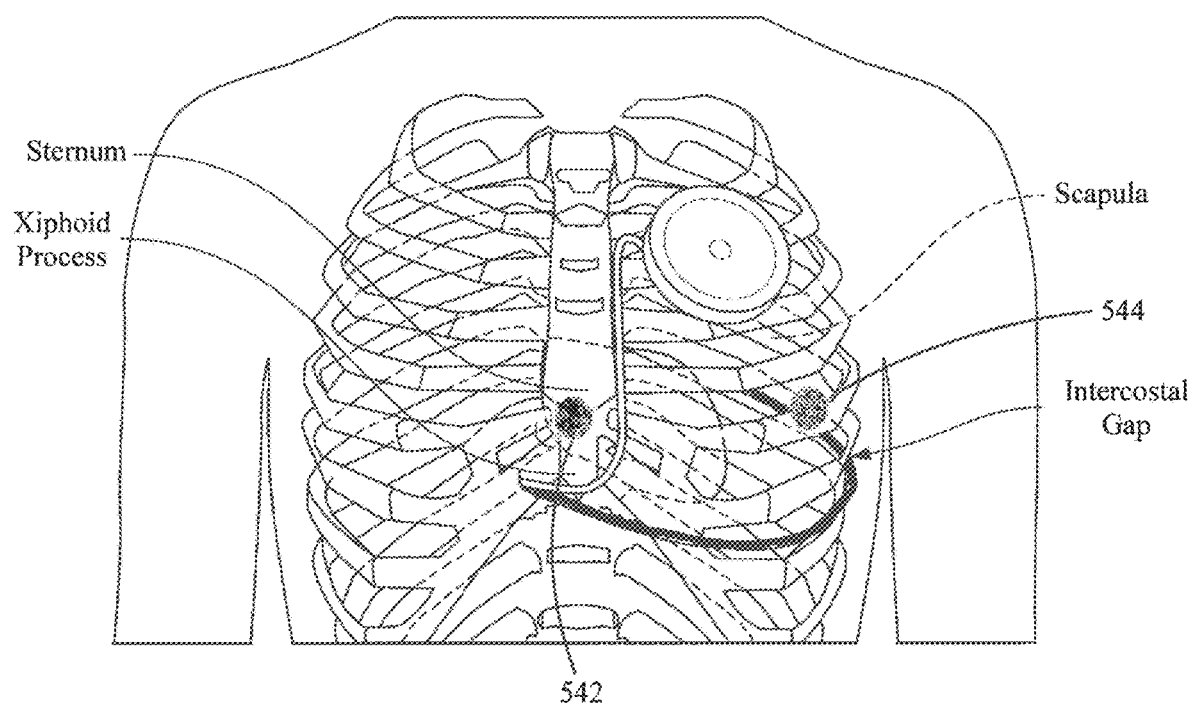
FIG. 5B illustrates the patient's torso and, particularly, the rib cage and the heart in accordance with embodiments herein.

FIG. 5B illustrates the patient's torso and, particularly, the rib cage and the heart. The implantable medical system includes a subcutaneous implantable device (SIMD) having a pulse generator positioned within a pocket of a pectoral region of a patient. The pocket may be a subcutaneous pocket positioned below subcutaneous tissue but above muscle tissue. In alternative embodiments, the pocket may be sub-muscular (e.g., beneath the pectoral muscle). The pulse generator includes a housing and/or electrode of the pulse generator. In the illustrated embodiment, a single lead is coupled to the pulse generator within the pocket. The lead includes a lead body and an elongated lead coil. As shown, the lead extends from the pocket in the pectoral region and extra-thoracically along the sternum (e.g., over the sternum or parasternally within one to three centimeters from the sternum). A proximal end of the elongated lead coil is located proximate to the xiphoid process. As shown, the proximal end is positioned along the anterior of the chest on a right side of the sternum. Thus, in some embodiments, the lead 110 may cross over a mid-sternal line that extends through a center of the sternum.

The elongated lead coil has an active length that is measured between the proximal end and a distal end. The active length represents a length of the electrode (e.g., a coil electrode) along the lead. As shown, the elongated lead coil extends from proximate to the xiphoid process, along the anterior and side of the patient within an intercostal gap, and along the posterior of the patient toward the spine. As such, the elongated lead coil may wrap about the chest or torso of the patient. The distal end may be positioned proximate to a scapula of the patient. For example, the distal end may be positioned within the intercostal gap and proximate to the tip or the inferior angle of the scapula. The distal end may be positioned between a midaxillary line and a posterior axillary line of the patient. The midaxillary line is a coronal line extending along a surface of the body passing through an apex of the axilla. The posterior axillary line is a coronal line extending parallel to the midaxillary line and through the posterior axillary skinfold. In some instances, the distal end may be positioned beyond the posterior axillary line of the patient.

The elongated lead coil may be characterized as having a first electrode segment that includes the proximal end, and a second electrode segment that includes the distal end. For embodiments in which the elongated lead coil extends substantially continuously from the proximal end to the distal end, the elongated lead coil may also have an intermediate electrode segment that extends between the first and second electrode segments. The first and second electrode segments and the intermediate segment may be indistinguishable such that the elongated coil extends continuously between the proximal end and the distal end. Alternatively, the intermediate electrode segment may be discrete with respect to the first and second electrode segments such that gaps or spacings exist between the electrode segments.

In some embodiments, at least one of the electrode segments is a shock coil and at least one of the electrode segments is a sensing electrode. In other embodiments, each of the first electrode segment, the second electrode segment, and the intermediate segment is a shock coil. In certain embodiments, the first electrode segment, the second electrode segment, and/or the intermediate segment are electrically common (have same polarity) with one another.

The configuration of FIG. 5B includes sensing electrodes 542 and 544 located at substantially similar positions to the V1 and V5/V6 electrodes of the 12 lead ECG system, or defining substantially similar sensing vectors. The sensing electrodes 542 and 544 may be provided at corresponding points along a shocking coil lead and/or provided within a separate sensing lead.

Figure 5C:
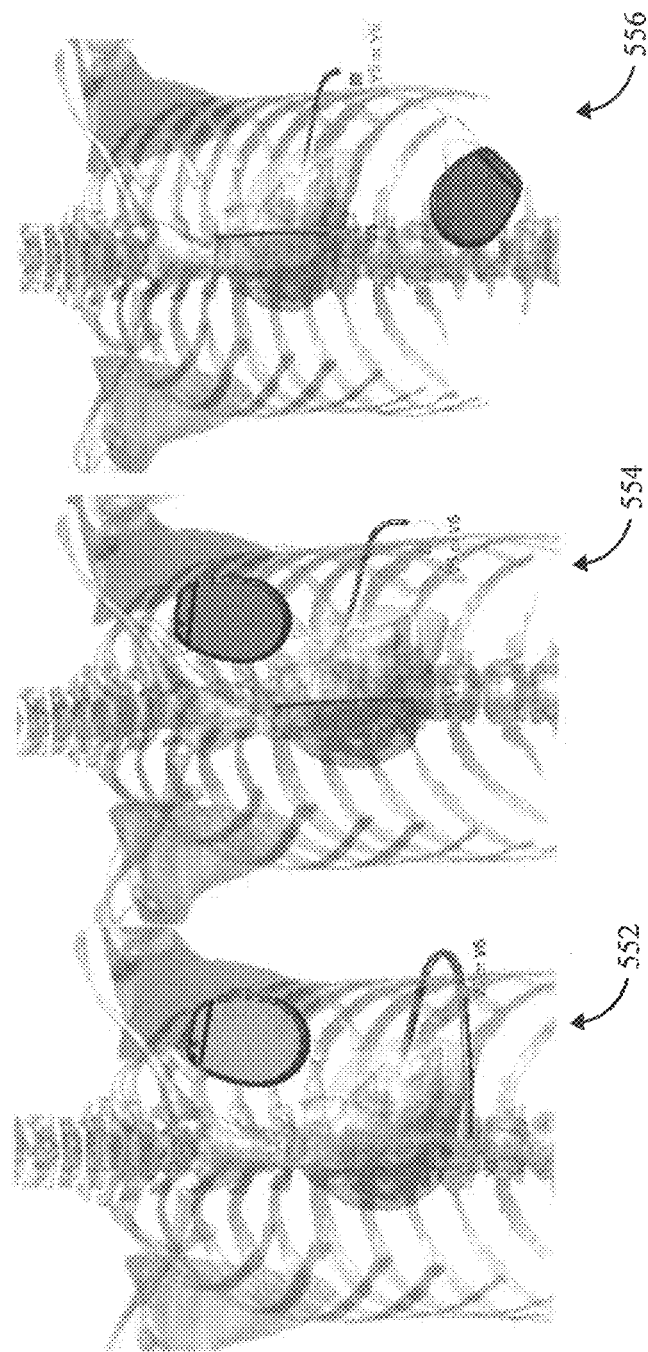
FIG. 5C illustrates examples for positions at which subcutaneous electrodes and a pectorally positioned subcutaneous S-IMD may be implanted in accordance with embodiments herein.

FIG. 5C illustrates examples for positions at which subcutaneous electrodes and a pectorally positioned subcutaneous S-IMD may be implanted in accordance with embodiments herein. The S-IMD system at 552 includes a single coil lead arranged to have a shocking coil positioned to extend along the anterior and side of the patient within an intercostal gap, and along the posterior of the patient toward the spine. The S-IMD is located at a pectoral pocket. At 554, the S-IMD and subcutaneous lead are inserted through a single common incision, as explained in one or more co-pending application incorporated herein. At 556, the S-IMD may be implanted in an abdominal position and the subcutaneous lead positioned along a posterior region. The S-IMD systems at 552-556 include subcutaneous electrodes positioned at substantially the same positions as the V1 electrode and the V5 or V6 electrodes.

Figure 6:
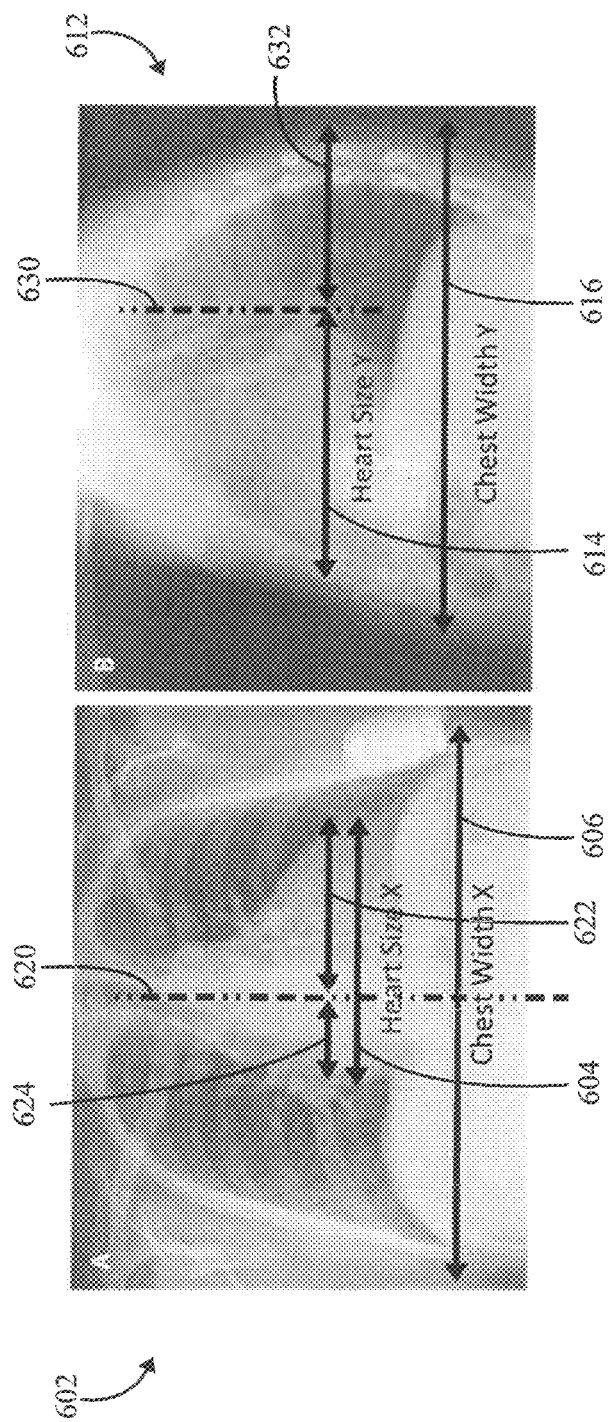
FIG. 6 illustrates front and side models of a torso to illustrate characteristics of cardiac dimensions that may be utilized in accordance with embodiments herein.

FIG. 6 illustrates front and side models of a torso to illustrate characteristics of cardiac dimensions that may be utilized in accordance with embodiments herein. At 602, a front model illustrates a heart having an AP dimension 604 in the X direction, and a patient chest AP dimension 606 in the X direction. Additionally or alternatively, the characteristics of the cardiac dimension may include a measure of a distance from a sternum center line 620 to the heart left wall 622 and a measure of a distance from the sternum center line 620 to the heart right wall 624. At 612, a side model illustrates a heart having a lateral dimension 614 in the Y direction, and a patient chest lateral dimension 616 in the Y direction. Additionally or alternatively, the characteristics of the cardiac dimension may include a measure of a distance 632 from a back wall of the heart 630 to a back of the patient's body. The cardiac dimensions may be measured In the AP and lateral directions and analyzed as characteristics of interest to supplement the characteristics of the CA signals in connection with identifying the LVH state. For example, the cardiac dimensions may be compared to cardiac dimension thresholds (associated with patients exhibiting a similar overall height and weight). For example, the analysis may compare the chest width and heart margins in AP view (X) and lateral view (Y) to reference heart and chest dimensions. The cardiac dimensions may be combined with the Sokolow-Lyon Product by calculating a product therebetween and/or a sum, to form an anatomy adjusted SLP.

Additionally or alternatively, the cardiac dimensions may be normalized or otherwise adjusted relative to the patient's torso dimensions. For example, a patient's chest dimensions may be measured in the AP and lateral directions and utilized to adjust the cardiac dimensions. Obese patients may exhibit higher DFTs, as compared to patients having a normal weight. The analysis may normalize or otherwise adjust the cardiac dimensions by determining ratios of the heart/chest dimensions and compare the ratio to one or more thresholds. For example, the ratio may compare the AP heart dimension to the AP chest dimension, and/or the lateral heart dimension to the lateral chest dimension. The ratios of the heart size X/chest size X and heart size Y/chest size Y may be combined with the Sokolow-Lyon Product by calculating a product therebetween and/or a sum, to form the anatomy adjusted SLP.

Calculation of DFT Expectation

Figure 7:
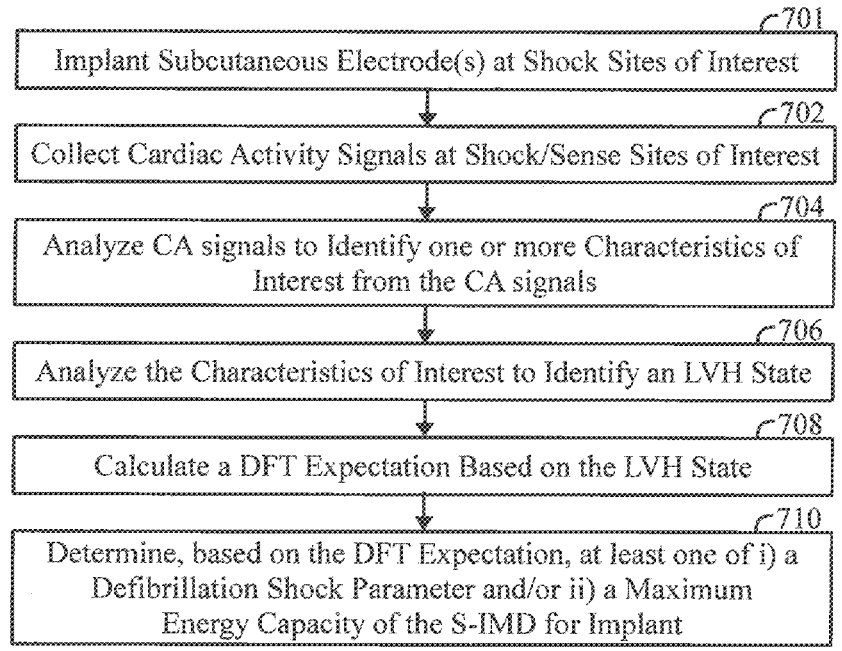
FIG. 7 illustrates a process for managing a subcutaneous implantable medical device based on left ventricular hypertrophy in accordance with embodiments herein.

FIG. 7 illustrates a process for managing a subcutaneous implantable medical device based on left ventricular hypertrophy in accordance with embodiments herein. The operations of FIG. 7 may be performed by one or more processors of an S-IMD, a local external device (e.g., during an implant procedure and/or post-implant by a bedside monitoring device), a remote server and the like.

At 701, one or more implantable (e.g., subcutaneous and/or transvenous) electrodes are implanted at corresponding shock sites of interest. The shock sites of interest define one or more shocking vectors through the myocardium. The implantable electrodes are positioned at sensing sites that are intended to serve as proxies or substitutes for surface sensing sites utilized by ECG leads, such as a 12 lead ECG system, examples of which are described herein. For example, the subcutaneous electrodes may be provided along a parasternal shocking coil, an anterior-posterior shocking coil, along separate sensing leads and the like. The subcutaneous electrodes may be positioned at a V1 sensing site, an V5 and/or V6 sensing site. Additionally or alternatively, transvenous electrodes may be located at select points within or proximate to the myocardium.

At 702, cardiac activity (CA) signals are collected from one or more implantable electrodes at corresponding sensing sites. For example, during an implant procedure, the CA signals may be collected after one or more implantable electrodes are implanted at sites corresponding to shock sites used to define shocking vectors. As another example, after an S-IMD system has been implanted, CA signals may be collected periodically and/or at the direction of a clinician or otherwise.

Before or during the operations of FIG. 7, one or more processors (e.g., of the IMD, local external device, remote server) may calibrate/correlate cardiac activity signals measured from the subcutaneous electrodes (also referred to as IEGM signals) to ECG signals collected by ECG electrodes at the 12 lead ECG positions discussed herein to form proxy CA signals. For example, the sensing vectors associated with subcutaneous or transvenous electrode configurations, may be correlated as proxies for sensing vectors, associated with surface ECG electrodes. For example, the cardiac activity signals sensed along subcutaneous or transvenous electrode vectors may be mathematically weighted and combined to form proxy cardiac activity signals.

At 704, one or more processors of the system analyze the CA signals to identify one or more characteristics of interest from the CA signals. Examples of various characteristics of interest are described herein. The CA signals are analyzed to identify different characteristics of interest dependent upon the criteria utilized. For example, when utilizing the Sokolow-Lyon Product, the CA signals at the V1 sensing site and the V5 or V6 sensing site are analyzed to identify peak voltages of the CA signals, such as a peak voltage of the R-wave. In addition, the duration of the QRS complex is measured from CA signals collected at one or more of the sensing sites (e.g., at V1, V5, V6, or elsewhere, or a combination thereof).

Additionally or alternatively, when the Cornell criteria are utilized, CA signals from implantable electrodes at the aVL and V3 sensing sites are analyzed to determine an amplitude of the R-wave at the aVL sensing site and an amplitude of the S-wave at the V3 sensing site. With the modified Cornell criteria, the R-wave, as measured at the aVL sensing site, is examined to identify the peak.

Additionally or alternatively, when the RE Scoring System criteria are utilized, the CA signals from the implantable electrodes are analyzed to identify amplitudes of the largest R-wave and S-wave are determined from the sensing sites of the limb leads, such as the three bipolar limb leads (I, II, and III) and three unipolar limb leads IV, V, and VI (also referred to as sensing vectors AVR, AVL, and AVF, respectively). The CA signal for the V1 or V to sensing site is analyzed for an amplitude of the S-wave. The CA signals for the V5 or V6 sensing sites are analyzed for the amplitude of the R-wave. The analysis also identifies: ST and T wave changes opposite QRS without digoxin, ST and T wave changes opposite QRS with digoxin, Left Atrial Enlargement. Left Axis Deviation, QRS duration, and intrinsicoid deflection in V5 or V6. The left atrial enlargement and left axial deviation may be entered separately by medical personnel.

Optionally, the analysis at 704 may further include determining cardiac dimensions of at least one of a heart or chest wall of the patient and updating the LVH state based on a characteristic of interest from the cardiac dimensions. For example, the one or more processors may receive measurements for cardiac dimensions in the AP and lateral directions. The processors analyze the characteristics of interest from the cardiac dimensions to supplement the characteristics of the CA signals in connection with identifying the LVH state. For example, the cardiac dimensions may be combined with the Sokolow-Lyon Product by calculating a product therebetween and/or a sum, to form an anatomy adjusted SLP. Additionally or alternatively, the cardiac dimensions may be compared to cardiac dimension thresholds (associated with patients exhibiting a similar overall height and weight). Based on the relation between the cardiac dimensions and the threshold, the SLP may be incremented or decremented a predetermined amount or an amount based on the relation between the cardiac dimensions in the threshold.

Additionally or alternatively, the cardiac dimensions may be normalized or otherwise adjusted relative to the patient's torso dimensions before being combined with the SLP. For example, a patient's chest dimensions may be measured in the AP and lateral directions. Obese patients may exhibit higher DFTs, as compared to patients having a normal weight. The analysis may normalize or otherwise adjust the cardiac dimensions by determining ratios of the heart/chest dimensions. The ratio may be used to increase or decrease the SLP such as through a mathematical relation. The ratios of the heart size X/chest size X and heart size Y/chest size Y may be combined with the Sokolow-Lyon Product by calculating a product therebetween and/or a sum, to form the anatomy adjusted SLP. Optionally, the analysis may compare the ratio to one or more thresholds. For example, the ratio may compare the AP heart dimension to the AP chest dimension, and/or the lateral heart dimension to the lateral chest dimension. In accordance with the foregoing, the LVH state is determined, such as based on the SLP alone and/or in combination with the cardiac dimensions. At 706, the one or more processors analyze the characteristics of interest from the CA signals to identify an LVH state. The CA signals analyzed at 706 may represent proxy CA signals that are derived from combining the CA signals sensed by the subcutaneous electrodes. Additionally or alternatively, the analysis may be applied to CA signals that are sensed by surface electrodes. Additionally or alternatively, the analysis may be applied to a combination of CA signals that are sensed by surface electrodes and CA signals that are sensed by the subcutaneous electrodes. Optionally, the operation at 706 may be implemented at different points in the process of FIG. 7, and not just after the operations at 704.

Various examples are described herein for criteria that may be utilized to determine when an LVH state is present. For example, the LVH state may be indicative of at least one of an occurrence or a degree of LVH experienced by the patient. The analysis may differ depending upon which criteria are utilized. For example, when utilizing the SLP protocol, the peak voltages for the R-wave, as measured at the V1 sensing site and V5 or V6 sensing sites are summed. The sum of the V1+(V5 or V6) is multiplied by the duration of the QRS complex to form an SLP value. The SLP value is compared to one or more thresholds.

Additionally or alternatively, when utilizing the Cornell criteria, the analysis includes adding together an amplitude of the R-wave (at the aVL sensing site) and an amplitude of the S-wave (at the V3 sensing site). The LVH state is set to be present or not present based upon whether the sum is greater than a predetermined amount (which may differ for male and female patients), such as greater than 28 mm for males and greater than 20 mm for females. With the modified Cornell criteria, the analysis determines whether the peak of the R-wave, as measured at the aVL sensing site, exceeds a predetermined threshold (e.g., 12 mm in amplitude), and if so, and LVH state is present.

Additionally or alternatively, when using the RE Scoring System, the following characteristics of CA signals are analyzed and assigned the corresponding point scores: Amplitude of largest R or S in limb leads≥20 mm=3 points, Amplitude of S in V1 or V2≥30 mm=3 points, Amplitude of R in V5 or V6≥30 mm=3 points, ST and T wave changes opposite QRS without digoxin=3 points, ST and T wave changes opposite QRS with digoxin=1 point, Left Atrial Enlargement=3 points, Left Axis Deviation=2 points, QRS duration≥90 ms=1 point, and intrinsicoid deflection in V5 or V6>50 ms=1 point. Based on the total score, the LVA state is set to be present or not present.

The foregoing examples set the LVH state in a binary manner, namely to be present or not present. Additionally or alternatively, the LVH state may be assigned a value along a scale, where a low value indicates a very small progression of LVH and/or a low likelihood that the patient is experiencing LVH, and where a high value along the scale indicates an advanced progression of LVH and/or a high likelihood that the patient is experiencing LVH. For example, an LVH scale may be defined between 0 and 10, with the LVH state set along the scale based on the value of the Sokolow-Lyon Product along a similar SLP scale. By way of example, the SLP may range between 20 uV-sec to 1000 uV-sec, or some other range. The SLP range may be normalized relative to an LVH range. For example, when the SLP value is 20 uV-sec to 300 uV-sec, the LVH scale may be set to 0-3, whereas when the SLP value is 700 uV-sec to 1000 uV-sec, the LVH scale may be set to 7-10.

At 708, the one or more processors calculate a DFT expectation based on the LVH state. Examples of various methods for calculating DFT expectations are described herein. One or more of the methods may be utilized alone or in combination when calculating the DFT expectation. The DFT expectation is representative of an estimate or likelihood that a patient would exhibit a particular defibrillation threshold and/or a defibrillation threshold within a select range. For example, when the LVH state is set to be present, the DFT expectation may be set to have a high DFT (e.g., greater than a DFT threshold). Alternatively, when the LVH state is set to be not present, the DFT expectation may be said to have a low DFT (e.g., less than the DFT threshold). For example, when the DFT expectation represents a discrete number (e.g., 20 J, 25 J, etc.), when the LVH state is not present, the DFT expectation may be set to 15 J, and when the LVH date is present, the DFT expectation may be set to 45 J.

Additionally or alternatively, when the LVH state is assigned a value along a range, the DFT expectation may be similarly assigned a DFT expectation along a range (e.g., a discrete value between 15 J and 45 J). Optionally, the DFT expectation may assign a range based on the LVH state. For example, when the LVH state is assigned a value of 4 along a range of 0-10, the DFT expectation may be assigned a range of 10-20 J. When the LVH state is assigned a value of 8 along a range of 0-10, the DFT expectation may be assigned a range of 30-40 J. Additionally or alternatively, the DFT expectation may be assigned a discrete value with a tolerance range (e.g., 15 J+/−5 J, 20 J+/−2 J) based on the LVH state. Additionally or alternatively, the DFT expectation may designate a discrete number, a range and/or a discrete value with a tolerance, along with a probability or likelihood that the value is accurate (e.g., 90% likely that the DFT is 10 J+/−2 J; 80% likely that the DFT is 15-25 J).

At 710, the one or more processors determine, based on the DFT expectation, at least one of i) a defibrillation shock parameter or ii) a maximum energy capacity of the S-IMD for implant. For example, when the processors determine a defibrillation shock parameter, the parameter may represent an energy level of a defibrillation shock to be delivered. Optionally, the processors may add a safety margin to the energy level otherwise indicated by the DFT expectation (e.g., energy output at DFT+5 J). Optionally, the processors may add a back-up shock to be delivered at a higher energy level (e.g., a maximum energy level), in the event that the medium energy shock does not terminate a defibrillation episode. As a further example, the operations of FIG. 7 may be implemented post-implant periodically throughout operation of an S-IMD, with the operation at 710 used to adjust the energy level of a defibrillation shock and a back-up shock. For example, when the DFT expectation is below a threshold, the processors within the S-IMD may adjust the energy level to charge the capacitor banks and deliver an MV shock. Over time, a patient's condition may deteriorate and the degree of LVH may progress, in which case the DFT expectation may increase to a level above the threshold. As LVH progresses, the S-IMD may compensate accordingly by adjusting the energy level from an initial lower level to a higher level (e.g., from an MV shock to a HV shock), such as when the LVH state exceeds an LVH threshold. In the foregoing example, the one or more processors of the S-IMD automatically perform the identifying, analyzing, calculating and determining operations at 704-710 after implantation, on a periodic basis in order to monitor progression of the LVH condition.

Additionally or alternatively, the identifying, analyzing, calculating and determining operations at 704-710 may be performed during an implantation procedure by one or more processors of an S-IMD, a local external device (e.g., a programmer device) and/or a remote server located at the medical facility or elsewhere. The determining operation may be performed automatically by the one or more processors and/or manually by a physician, when reviewing the results of the calculation of the DFT expectation. When performed during an implant procedure, the determination may include determining the maximum energy capacity needed for, or warranted by, the S-IMD for implant. For example, a group of S-IMDs may be present and available to the physician for implant, where each of the S-IMDs have different maximum energy capacities. For example, the group may include at least first and second test-S-IMDs having corresponding different first and second maximum energy capacities, such as when the first S-IMD has a maximum energy capacity of 48 J (and thus is more suitable for patients with lower DFT expectations), while the second S-IMD may have a maximum energy capacity of 80 jewels (and thus is more suitable for patients with higher DFT expectations).

Optionally, the operations of FIG. 7 may represent a post-implant monitoring process. In connection therewith, sensing electrodes of the S-IMD system are used to collect CA signals at sensing sites utilized in connection with left ventricular hypertrophy monitoring (e.g., the V1, V5, V6 sensing sites, etc.). The CA signals may be analyzed in accordance with a corresponding LVH analysis method (e.g., the Sokolow-Lyon Product method). Optionally, the results of the LVH analysis may be combined with stored patient anatomy the data, such as cardiac dimensions and chest dimensions previously entered by a clinician. The LVH state and/or DFT expectations may be recorded periodically over time, and at predetermined times wirelessly downloaded from the S-IMD to a local external device, home care network monitor, remote server and the like. Additionally or alternatively, the S-IMD may also record other information, such as the ST segment width and elevation, QRS width, heart failure and the like. The LVH states and DFT expectations that are recorded over time may be utilized to show a trend and progression of LVH. For example, when a patient is undergoing a drug treatment and other therapy, the LVH states and DFT expectations may be used to monitor progression of the LVH with respect to the drug treatment, thereby providing information indicating whether the drug therapy is helpful or has no effect.

Optionally, in the event that the LVH state and/or DFT expectation crosses a threshold indicating that the patient is entering a high risk state for a high DFT, the S-IMD may issue a warning. For example, the warning may be issued through a local external device and/or remote patient care system at the patient's home. Additionally or alternatively, the warning may be issued through a local external device and/or remote patient care system to a physician's office or remote server of a medical network. The warning may include various indications, such as an amount of change in the DFT expectation. The warning may indicate that the patient should schedule a visit with the attending physician and the like.

In accordance with embodiments herein, the processes described herein may be utilized to automatically change and energy level of defibrillation shocks. For example, the S-IMD may be programmed at 25 J when a patient is tested and the DFT expectation meet certain criteria. If the results from the LVH monitoring described herein indicate an increased risk of an elevated DFT, the S-IMD may automatically change the energy level for the relation shocks to a greater programmed energy level, such as 45 J.

Modeling DFT Expectation

Figure 8:
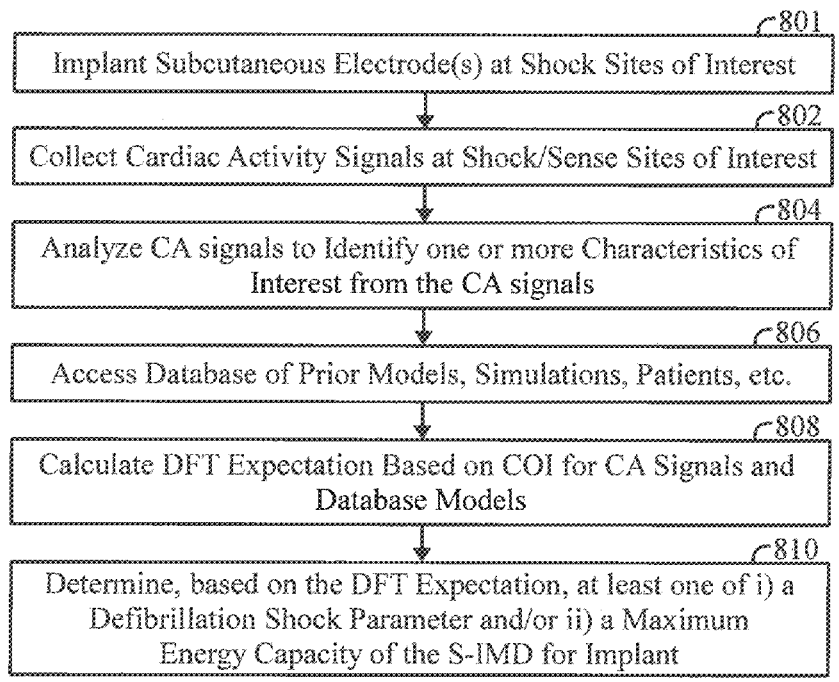
FIG. 8 illustrates a process for managing a subcutaneous implantable medical device based on left ventricular hypertrophy and a database constructed from model simulations of human body models, CA signal characteristics of interest and the like, in accordance with embodiments herein.

FIG. 8 illustrates a process for managing a subcutaneous implantable medical device based on left ventricular hypertrophy and a database constructed from model simulations of human body models, CA signal characteristics of interest and the like, in accordance with embodiments herein. The operations of FIG. 8 may be performed by one or more processors of an S-IMD, a local external device (e.g., during an implant procedure and/or post-implant by a bedside monitoring device), a remote server and the like.

At 801, one or more implantable electrodes are implanted at corresponding shock sites of interest. At 802, cardiac activity (CA) signals are collected from one or more implantable electrodes at corresponding sensing sites. Before or during the operations of FIG. 8, cardiac activity signals measured from the subcutaneous electrodes may be correlated to ECG signals collected by ECG electrodes. For example, the cardiac activity signals sensed along subcutaneous electrode vectors may be mathematically weighted and combined to form proxy cardiac activity signals.

At 804, one or more processors of the system analyze the CA signals to identify one or more characteristics of interest from the CA signals. At 806, the one or more processors access a database that has been previously constructed from prior patient data and/or model simulations. For example, prior patient data may be added to the database recording information such as cardiac dimensions, chest dimensions, CA signal characteristics of interest (corresponding to one or more desired methods for identifying LVH), the patient's DFT expectation and the patient's actual DFT. The database may maintain a patient's actual DFT at the time of implant, as well as at various times throughout the time period in which an S-IMD is implanted. Additionally or alternatively, the database may be built with model simulations constructed for various human body models, characteristics of interest from CA signals and the like. At 808, the one or more processors analyze the characteristics of interest from the CA signals and the information from the database to identify an LVH state. By way of example, an individual patient's cardiac dimensions and/or CA signal measurements for characteristics of interest may be utilized to access a database. The patient's dimensions and CA signal measurements maybe then used to extrapolate a point into the database to identify an LVH state and a DFT expectation. At 808, the one or more processors calculate the DFT expectation based on the LVH state. Examples of various methods for calculating DFT expectations are described herein.

At 810, the one or more processors determine, based on the DFT expectation, at least one of i) a defibrillation shock parameter or ii) a maximum energy capacity of the S-IMD for implant. For example, when the processors determine a defibrillation shock parameter, the parameter may represent an energy level of a defibrillation shock to be delivered. Optionally, the processors may add a safety margin to the energy level otherwise indicated by the DFT expectation (e.g., energy output at DFT+5 J). Optionally, the processors may add a back-up shock to be delivered at a higher energy level (e.g., a maximum energy level), in the event that the medium energy shock does not determine a defibrillation episode. As a further example, the operations of FIG. 8 may be implemented post-Implant periodically throughout operation of an S-IMD, with the operation at 810 being used to adjust the energy level of a defibrillation shock and a back-up shock. For example, when the DFT expectation is below a threshold, the processors may adjust the energy level to deliver and MV shock. Over time, a patient's condition may deteriorate and the degree of LVH may progress, in which case the DFT expectation may increase to a level above the threshold. As LVH progresses, the S-IMD may compensate accordingly by adjusting the energy level from an initial lower MV shock to a higher HV shock, such as when the LVH state exceeds and LVH threshold. In the foregoing example, the one or more processors of an S-IMD automatically perform the identifying, analyzing, calculating and determining operations at 804-810 after implantation, on a periodic basis in order to monitor progression of the LVH condition.

Additionally or alternatively, the identifying, analyzing, calculating and determining operations at 804-810 may be performed during an implantation procedure by one or more processors of an S-IMD, a local external device (e.g., a programmer device) and/or a remote server located at the medical facility or elsewhere. The determining operation may be performed automatically by the one or more processors and/or manually by a physician, when reviewing the results of the calculation of the DFT expectation. When performed during an implant procedure, the determination may include determining the maximum energy capacity needed for or warranted by the S-IMD for implant. For example, a group of S-IMDs may be present and available to the physician for implant, where each of the S-IMDs have different maximum energy capacities. For example, the group may include at least first and second test-S-IMDs having corresponding different first and second maximum energy capacities, such as when the first S-IMD has a maximum energy capacity of 48 J (and thus is more suitable for patients with lower DFT expectations), while the second S-IMD may have a maximum energy capacity of 80 jewels (and thus is more suitable for patients with higher DFT expectations).

In accordance with the operations of FIG. 8, embodiments herein utilize a database of prior patients or model simulations and measurements from a current patient to extrapolate points into the database to identify a DFT expectation for a current patient. From the DFT expectation, the parameters for the defibrillation shock may be set. Additionally or alternatively, different size S-IMDs may be chosen between for implant based on the DFT expectation and the energy capacity of the various S-IMDs.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored In a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be In the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated In the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used In combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for managing an implantable medical device (IMD) based on left ventricular hypertrophy (LVH), the method comprising:
    collecting cardiac activity (CA) signals from one or more implantable electrodes at corresponding sensing sites;
    utilizing one or more processors to perform:
        identifying a characteristic of interest from the CA signals;
        analyzing the characteristic of interest from the CA signals to identify an LVH state indicative of at least one of an occurrence or degree of LVH experienced by the patient;
        calculating a defibrillation threshold (DFT) expectation based on the LVH state; and
        determining, based on the DFT expectation, at least one of i) a defibrillation shock parameter or ii) a maximum energy capacity of the IMD for implant.

2. The method of claim 1, wherein the determining comprises determining, as the defibrillation shock parameter, an energy level of a defibrillation shock.

3. The method of claim 2, further comprising obtaining an LVH threshold and automatically adjusting the energy level of the defibrillation shock from a medium voltage (MV) shock to a high voltage (HV) shock when the LVH state exceeds the LVH threshold.

4. The method of claim 1, wherein the one or more processors are provided within the IMD and wherein the identifying, analyzing, calculating and determining operations are performed automatically by the one or more processors, after implantation, on a periodic basis to monitor progression of the LVH.

5. The method of claim 1, wherein the identifying, analyzing and calculating operations are performed during an implantation procedure for implanting the IMD and wherein the determining comprises determining the maximum energy capacity of the IMD for implant.

6. The method of claim 5, further comprising selecting, based on the DFT expectation, between at least first and second IMDs having corresponding different first and second maximum energy capacities.

7. The method of claim 1, wherein the implantable electrodes are positioned at i) a V1 sensing site and a V5 sensing site or ii) the V1 sensing site and a V6 sensing site.

8. The method of claim 1, further comprising determining cardiac dimensions of at least one of a heart or chest wall of the patient and updating the LVH state based on a characteristic of interest from the cardiac dimensions.

9. The method of claim 1, wherein the calculating the DFT expectation is based in part on model simulations recorded in a database.

10. The method of claim 1, wherein the analyzing operation utilizes a Sokolov-Lyon Product to identify when a patient is experiencing LVH or not experiencing LVH as the LVH state.

11. A system for managing an implantable medical device (IMD) based on left ventricular hypertrophy (LVH), the system comprising:
    electrodes configured to collect cardiac activity (CA) signals at corresponding sensing sites;
    one or more processors configured to:
        identify a characteristic of interest from the CA signals;
        analyze the characteristic of interest from the CA signals to identify an LVH state indicative of at least one of an occurrence or degree of LVH experienced by the patient;
        calculate a defibrillation threshold (DFT) expectation based on the LVH state; and
        determine, based on the DFT expectation, at least one of i) a defibrillation shock parameter or ii) a maximum energy capacity of the IMD for implant.

12. The system of claim 11, wherein the one or more processors are further configured to determine, as the defibrillation shock parameter, an energy level of a defibrillation shock.

13. The system of claim 12, wherein the one or more processors are further configured to automatically adjust the energy level of the defibrillation shock from a medium voltage (MV) shock to a high voltage (HV) shock when the LVH state exceeds an LVH threshold.

14. The system of claim 11, wherein the one or more processors are provided within a subcutaneous implantable medical device (S-IMD) and wherein the identify, analyze, calculate and determine operations are performed automatically by the one or more processors, after implantation, on a periodic basis to monitor progression of the LVH.

15. The system of claim 11, wherein the identify, analyze and calculate operations are performed during an implantation procedure for implanting an implantable medical device (IMD) and wherein the determine comprises determining the maximum energy capacity of the IMD for implant.

16. The system of claim 15, wherein the one or more processors are further configured to select, based on the DFT expectation, between at least first and second IMDs having corresponding different first and second maximum energy capacities.

17. The system of claim 11, wherein the implantable electrodes are positioned at i) a V1 sensing site and a V5 sensing site or ii) the V1 sensing site and a V6 sensing site.

18. The system of claim 11, wherein the one or more processors are further configured to receive cardiac dimensions of at least one of a heart or chest wall of the patient and update the LVH state based on a characteristic of interest from the cardiac dimensions.

19. The system of claim 11, wherein the one or more processors are further configured to calculate the DFT expectation based in part on model simulations recorded in a database.

20. The system of claim 11, wherein the one or more processors are configured to perform the analyze operation utilizing a Sokolow-Lyon Product to identify when a patient is experiencing LVH or not experiencing LVH as the LVH state.

\* \* \* \* \*